(12) United States Patent
Farra

(10) Patent No.: US 9,919,103 B2
(45) Date of Patent: Mar. 20, 2018

(54) IMPLANTABLE MEDICAL DEVICE FOR MINIMALLY-INVASIVE INSERTION

(71) Applicant: MicroCHIPS, Inc., Lexington, MA (US)

(72) Inventor: Robert Farra, Acton, MA (US)

(73) Assignee: MICROCHIPS BIOTECH, INC., Lexington, MA (US)

( * ) Notice: Subject to any disclaimer, the term of this patent is extended or adjusted under 35 U.S.C. 154(b) by 326 days.

(21) Appl. No.: 14/135,782

(22) Filed: Dec. 20, 2013

(65) Prior Publication Data

US 2014/0180262 A1 Jun. 26, 2014

Related U.S. Application Data

(60) Provisional application No. 61/745,086, filed on Dec. 21, 2012.

(51) Int. Cl.
| | |
|---|---|
| *H05K 5/00* | (2006.01) |
| *A61M 5/172* | (2006.01) |
| *A61B 5/07* | (2006.01) |
| *A61B 5/00* | (2006.01) |

(52) U.S. Cl.
CPC ............ *A61M 5/172* (2013.01); *A61B 5/076* (2013.01); *A61B 5/4839* (2013.01); *A61B 2562/166* (2013.01); *H01L 2224/48091* (2013.01); *H01L 2224/48227* (2013.01); *Y10T 29/4913* (2015.01)

(58) Field of Classification Search
CPC ............ H05K 3/36; H01L 2224/48091; H01L 2924/00014; H01L 2224/48227; A61B 2562/166; A61B 5/076; A61B 5/4839; A61M 5/172; Y10T 29/4913

USPC ............ 361/752; 600/377; 604/891; 29/830; 156/242; 228/180.5

See application file for complete search history.

(56) References Cited

U.S. PATENT DOCUMENTS

| | | |
|---|---|---|
| 5,782,891 A | 7/1998 | Hassler et al. |
| 6,052,623 A | 4/2000 | Fenner et al. |
| 6,123,861 A | 9/2000 | Santini, Jr. et al. |
| 6,491,666 B1 | 12/2002 | Santini, Jr. et al. |
| 6,527,762 B1 | 3/2003 | Santini, Jr. et al. |
| 6,551,838 B2 | 4/2003 | Santini, Jr. et al. |

(Continued)

FOREIGN PATENT DOCUMENTS

EP 1540727 B1 10/2010

*Primary Examiner* — Yuriy Semenenko

(74) *Attorney, Agent, or Firm* — Eversheds Sutherland (US) LLP

(57) ABSTRACT

Containment devices and methods of manufacture and assembly are provided. In an embodiment, the containment device includes an elongated microchip element comprising one or more containment reservoirs that are configured to be electrically activated to open. The containment device also include an elongated electronic printed circuit board (PCB) comprising a substrate. The elongated PCB comprises a first side on which one or more electronic components are fixed and an opposed second side on which the elongated microchip element is fixed in electrical connection to the one or more electronic components. Further, the containment device includes an elongated housing fixed to the elongated PCB. The elongated housing is configured to hermetically seal the one or more electronic components of the elongated PCB within the elongated housing.

28 Claims, 6 Drawing Sheets

(56) References Cited

U.S. PATENT DOCUMENTS

| | | |
|---|---|---|
| 6,773,429 B2 | 8/2004 | Sheppard, Jr. et al. |
| 6,808,522 B2 | 10/2004 | Richards et al. |
| 6,827,250 B2 | 12/2004 | Uhland et al. |
| 6,875,208 B2 | 4/2005 | Santini, Jr. et al. |
| 6,976,982 B2 | 12/2005 | Santini, Jr. et al. |
| 7,070,590 B1 | 7/2006 | Santini, Jr. et al. |
| 7,114,312 B2 | 10/2006 | Coppeta et al. |
| 7,226,442 B2 | 6/2007 | Sheppard, Jr. et al. |
| 7,354,597 B2 | 4/2008 | Johnson et al. |
| 7,413,846 B2 | 8/2008 | Maloney et al. |
| 7,488,316 B2 | 2/2009 | Prescott et al. |
| 7,497,855 B2 | 3/2009 | Ausiello et al. |
| 7,510,551 B2 | 3/2009 | Uhland et al. |
| 7,534,241 B2 | 5/2009 | Coppeta et al. |
| 7,537,590 B2 * | 5/2009 | Santini, Jr. ........... A61K 9/0009 604/890.1 |
| 7,599,737 B2 | 10/2009 | Yomtov et al. |
| 7,604,628 B2 | 10/2009 | Santini, Jr. et al. |
| 7,917,208 B2 * | 3/2011 | Yomtov ............ A61M 5/14276 607/120 |
| 8,095,197 B2 | 1/2012 | Santini, Jr. et al. |
| 8,191,756 B2 | 6/2012 | Coppeta et al. |
| 8,604,810 B2 | 12/2013 | Sheppard, Jr. et al. |
| 8,649,840 B2 | 2/2014 | Sheppard, Jr. et al. |
| 2002/0187260 A1 * | 12/2002 | Sheppard et al. ......... 427/248.1 |
| 2003/0034564 A1 | 2/2003 | Palanisamy et al. |
| 2004/0247671 A1 * | 12/2004 | Prescott ............... A61K 9/0009 424/468 |
| 2006/0076236 A1 | 4/2006 | Shah et al. |
| 2006/0115323 A1 * | 6/2006 | Coppeta et al. .............. 403/270 |
| 2006/0171989 A1 * | 8/2006 | Prescott ............... A61K 9/0024 424/426 |
| 2010/0119604 A1 | 5/2010 | Prescott et al. |
| 2010/0149042 A1 | 6/2010 | Utsi et al. |
| 2012/0035528 A1 | 2/2012 | Coppeta et al. |
| 2012/0130339 A1 | 5/2012 | Farra |
| 2013/0053671 A1 | 2/2013 | Farra |
| 2013/0211219 A1 | 8/2013 | Coppeta et al. |

* cited by examiner

IMPLANTABLE MEDICAL DEVICE FOR MINIMALLY-INVASIVE INSERTION

CROSS-REFERENCE TO RELATED APPLICATIONS

The present application claims priority to and the benefit of U.S. Provisional Patent Application No. 61/745,086, filed Dec. 21, 2012, which is hereby incorporated by reference in its entirety.

FIELD OF THE DISCLOSURE

The present disclosure relates generally to multi-reservoir containment devices, including but not limited to medical devices, such as implantable medical devices, having containment reservoirs for confining substance or subcomponents for precisely controlled exposure or release. In certain aspects, the present disclosure relates to improved designs of such devices configured for insertion into a patient via minimally invasive instruments, such as trocars, catheters, injectors, and the like.

BACKGROUND

Typical implantable medical devices, such as pacemakers and implantable cardioverter defibrillators, are designed with two or more housing components or shells that contain the control electronics, power source, and other device specific components. A header is also used to provide electrical connections into and out of the device. The housing and header (or feedthrough) are designed to be hermetic to prevent liquid or gas exchange between the internal components (which are typically not biocompatible) and body fluids. It is noted, however, that certain implants with epoxy based headers do not achieve long term hermeticity. Design and manufacturing methods of implantable devices have evolved with the goal of ensuring hermeticity.

MicroCHIPS Inc. designs and manufactures implantable devices based on microchips that include reservoir arrays containing biosensors or drugs, for example. FIG. 1 shows a possible conventional approach for assembly of components in an implantable medical device 10, which includes a microchip assembly 12. The microchip assembly 12, which is also referred to as a microchip element, includes microreservoirs, each of which may contain a drug for controlled delivery in vivo or a sensor for controlled exposure in vivo. The microchip assembly 12 is attached to a feedthrough 16 that is welded to the housing 14. Such microchip assemblies or elements are described, for example, in U.S. Pat. No. 7,510,551 to Uhland et al. and U.S. Pat. No. 7,604,628 to Santini Jr. et al. The feedthrough 16 contains electrically conductive pins that are metallurgically brazed to metallized surfaces on and through an alumina disc. A typical pin count exceeds 100, and in more complex designs, can be over 400. The consequence of such designs is that each pin connection potentially can be a leak point.

In addition, each feedthrough pin is electrically connected to an electronic component inside the housing. Some designs utilize a wire from the pin to the circuit, while the illustrated design attaches the feedthrough 16 directly to a conventional plastic circuit board 18 (which generally would be unsuitable for continuous in vivo contact with the patient). These electrical connections require testing to ensure continuity. As a result, the pin count impacts the cost of the feedthrough, and that cost increases as the number of feedthrough pins increases in the implantable device. Consequently, due to this complex design requirement, the resulting manufacturing, and the required acceptance tests, the feedthrough is a relatively expensive component.

Another disadvantage of conventional implantable device designs based on a feedthrough or header attached to housing components is that the overall volume of the resulting device is larger than ideally desired, because several discrete components make up the assembly.

Furthermore, electronic-based implantable devices that use radio frequency to wirelessly transfer information in and out of the body require an antenna. Radio frequency waves are significantly attenuated when the antenna is placed in a conventional metallic housing, and therefore, the antenna typically is placed on the surface of the housing, utilizing the existing feedthrough or another feedthrough dedicated for this application.

It therefore would be desirable to eliminate or mitigate any or all of the foregoing disadvantages associated with conventional designs of implantable medical devices. In one particular need, it would be desirable to provide improved housing hermeticity (e.g., fewer potential leak paths), simpler construction, and a smaller overall device volume.

In conjunction with the desire to provide improved hermetic reservoir devices, it would also be advantageous to improve the manner in which such actively-controlled reservoir devices can be operably deployed into a patient in need thereof. For example, it would be desirable to reduce the size of incisions and/or increase the possible range of tissue sites into which the device can be suitably deployed without undue pain or discomfort to the patient. It would be desirable to provide device configurations conducive to such uses in patients.

SUMMARY

Some or all of the above needs and/or problems may be addressed by one or more embodiments described herein. In one embodiment, a containment device is provided that includes an elongated microchip element having one or more containment reservoirs that are configured to be electrically activated to open. The containment device also includes an elongated electronic printed circuit board (PCB) comprising a biocompatible substrate. The elongated PCB also comprises a first side on which one or more electronic components are fixed and an opposed second side on which the elongated microchip element is fixed in electrical connection to the one or more electronic components. Further, the containment device includes an elongated housing fixed to the elongated PCB. The elongated housing is configured to hermetically seal the one or more electronic components of the elongated PCB within the elongated housing.

Other embodiments, aspects, and features of the containment device will become apparent to those skilled in the art from the following detailed description, the accompanying drawings, and the appended claims.

BRIEF DESCRIPTION OF THE DRAWINGS

Reference will now be made to the accompanying drawings, which are not necessarily drawn to scale.

DETAILED DESCRIPTION

Illustrative embodiments will now be described more fully hereinafter with reference to the accompanying drawings, in which some, but not all embodiments are shown. The representative embodiments described in the disclosure may be embodied in many different forms and should not be construed as limited to the embodiments set forth herein. Like numbers refer to like elements throughout.

The containment devices and assemblies described herein provide, among other advantages, significantly improved space efficiency of the assembled devices. For example, compared with prior art devices, embodiments of the present devices can hold the same or a larger drug payload is the same or a smaller overall device volume. Moreover, in certain embodiments, the devices and methods advantageously eliminate the need for a costly and complex feedthrough, provide a thinner, sleek implant due to the elimination of the feedthrough, provide improved reliability by eliminating numerous feedthrough pins and electrical connections, provide improved reliability by reducing the number of hermetic interfaces, simplify tests to confirm functionality, and provide a simpler assembly. This can be particularly important in embodiments in which the containment device is an implantable medical device intended for long-term implantation in a human or animal subject via minimally-invasive insertion means, such as through a small incision, trocar, cannula, injector, or similar like medical instrument.

Figure 1:
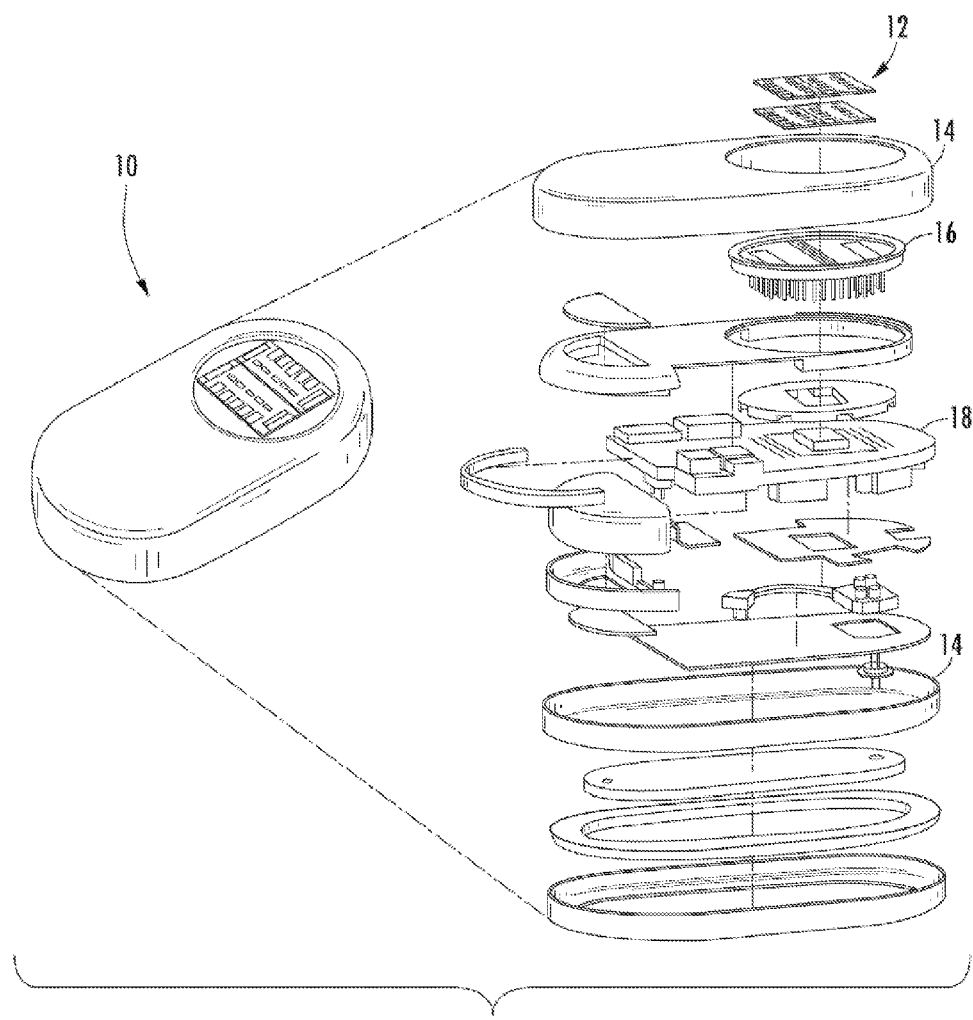
FIG. 1 schematically depicts an exploded perspective view of a prior art containment device including a microchip assembly.
Figure 2A:
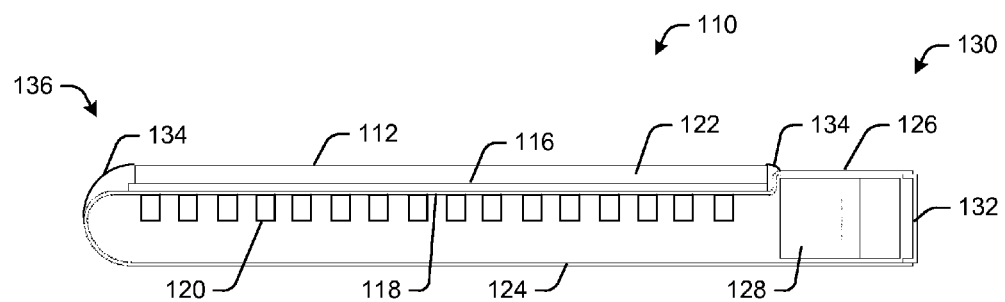
FIG. 2A schematically depicts a cross-sectional view of an assembled containment device including a microchip assembly according to an embodiment.
Figure 2B:
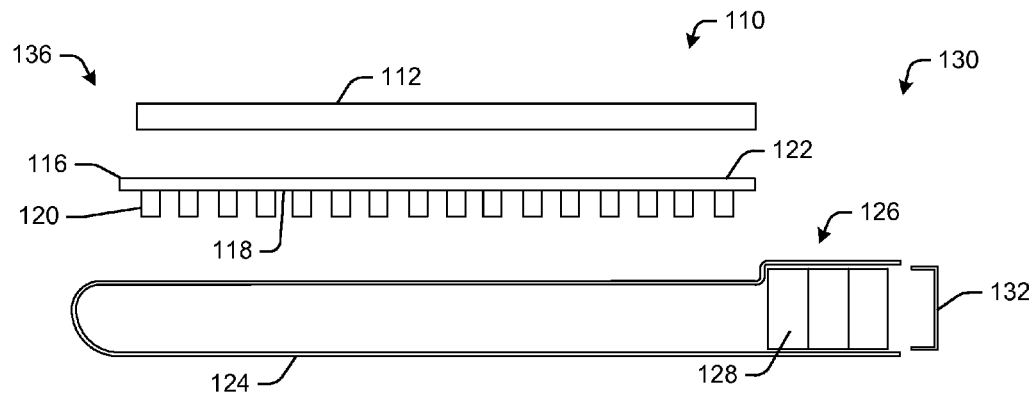
FIG. 2B schematically depicts an exploded cross-sectional view of the containment device shown in FIG. 2A.
Figure 2C:
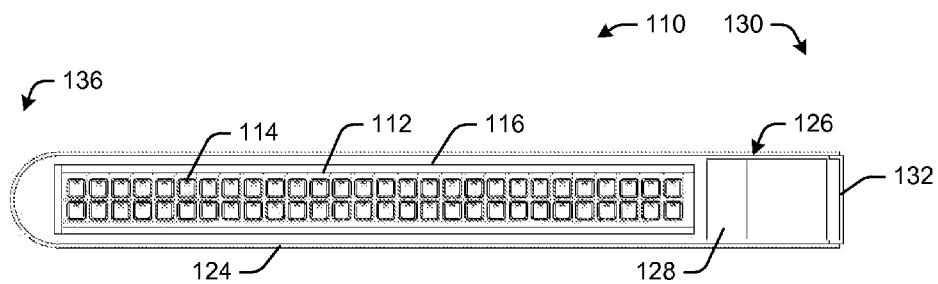
FIG. 2C schematically depicts a top view of the containment device shown in FIGS. 2A and 2B.
Figure 3:
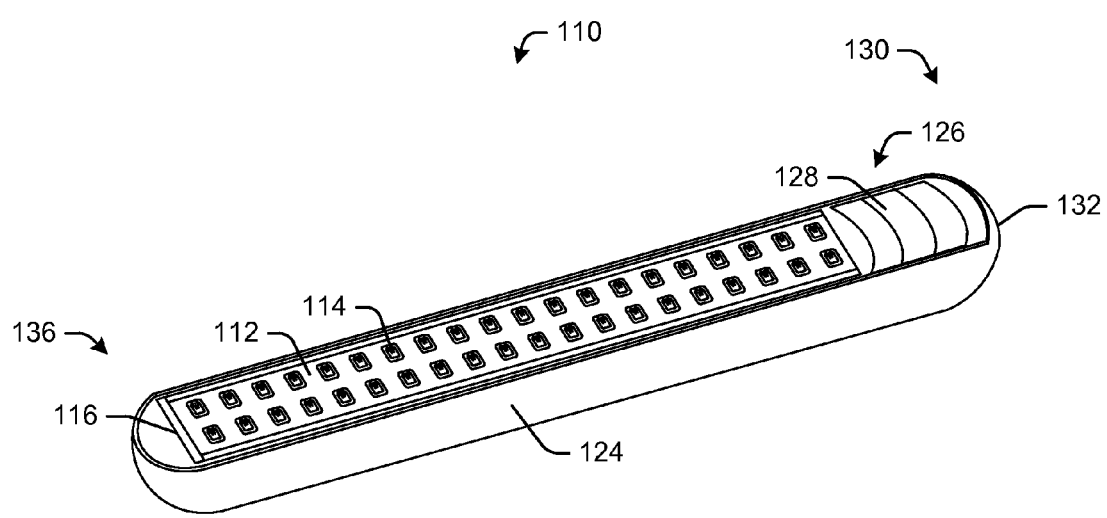
FIG. 3 schematically depicts a perspective view of the containment device illustrated in FIGS. 2A-2C.

The containment devices provided herein may be further understood with reference to the following exemplary embodiments, including the containment device 110 illustrated in FIGS. 2A-3. The containment device 110 includes an elongated microchip element 112 which comprises one or more containment reservoirs 114 that can be electrically activated to open. The containment device 110 also includes an elongated electronic printed circuit board (PCB) 116. The elongated PCB 116 comprises a biocompatible substrate and has a first side 118 on which one or more electronic components 120 are fixed and an opposed second side 122 on which the microchip element 112 is fixed in electrical connection to the one or more electronic components 120. As will be explained below with reference to FIG. 4, the electronic components 120 on the first side 118 of the PCB 116 are in electrical (i.e., operable) communication with the microchip element 112.

It is understood that the containment device 110 may include any suitable number of microchip elements 112 (e.g., from 1 to 6) and that each microchip element 112 may include a plurality of discrete containment reservoirs 114 (e.g., from 10 to 750 reservoirs). More microchip elements 112, and fewer or more containment reservoirs 114, per containment device 110 are also envisioned. Moreover, it is understood that the containment device 110 may include any suitable number of PCBs 116.

As shown in FIGS. 2A-2C, embodiments particularly suitable for minimally invasive insertion into a patient may have long, narrow microchip elements 112 with elongated arrays of closely spaced containment reservoirs. FIG. 2C shows a 2×28 reservoirs array. In one embodiment, the elongated array has from 1 to 4 rows of 20 to 40 reservoirs. In other embodiments, other numbers of rows and reservoirs are envisioned.

The "electronic printed circuit board" (PCB) refers to a substrate that mechanically supports and electrically connects electronic components using conductive pathways, tracks, or signal traces as known in the art. In embodiments, the PCB includes a biocompatible and hermetic substrate material. Suitable such materials include ceramics, such as alumina and silicon nitride. Multi-layer alumina PCBs have been successfully designed and manufactured. See, for example, U.S. Patent Application Publication No. 2003/0034564. These laminations may be the result of combining conductive layers, dielectric layers, and aluminum oxide ($Al_2O_3$, alumina) in a low temperature co-fired process. The alumina is referred to as low temperature co-fired ceramic (LTCC). These biocompatible ceramics also function as a hermetic barrier, eliminating the need, in some instances, for conventional metallic housing elements. Other materials or combinations of materials capable of performing all or some of the described function may also be used.

The term "biocompatible" as used herein generally refers to materials of construction that are suitable for long-term or short-term implantation into a human or animal subject, e.g., a patient. Such materials of constructions are known in the art of implantable medical devices.

As used herein, the term "hermetic seal" refers to preventing undesirable ingress or egress of chemicals (e.g., water vapor, water, oxygen, etc.) into or from one or more compartments of the device, such as the device reservoirs or housings, over the useful life of the device. For purposes herein, a material/seal that transmits helium (He) at a rate less than $1 \times 10^{-9}$ atm*cc/sec is termed hermetic.

The containment device 110 may include an elongated housing 124. The elongated housing 124 is configured to hermetically seal the one or more electronic components 120 of the elongated PCB 116 within the elongated housing 124. That is, the elongated housing 124 is configured to surround the first side 118 of the elongated PCB 116. In this manner, the elongated housing 124 and the elongated PCB 116 collectively form a hermetic enclosure around the one or more electronic components 120. Desirably, the elongated housing 124 and at least a portion of the outward facing second side 122 of the elongated PCB 114 are formed of a biocompatible material. For example, in some instances, the elongated housing 124 may be made of a biocompatible metal or alloy, such as titanium or stainless steel. In other instances, the elongated housing 124 may be made of a biocompatible polymer. In certain embodiments, at least a portion of the elongated housing 124 has a generally cylindrical body. In some instances, the elongated housing 124 includes atraumatic surfaces. Moreover, a distal end 136 of the elongated housing 124 may be rounded.

The elongated housing 124 may comprise a battery chamber 126 configured to house one or more batteries 128 therein. Any power source or power system may be housed within the battery chamber 126. In some instances, the battery chamber 126 may be a separate area within the elongated housing 124. In other instances, the battery chamber 126 may be part of a single enclosure formed by the elongated housing 124. In one embodiment, the battery chamber 126 may be positioned about a proximal end 130 of the elongated housing 124. However, the battery chamber 126 may be located at any position within the elongated housing 124. Moreover, in some instances, the battery chamber 126 may be omitted. For example, the device power may be provided by inductive charging.

In certain embodiments, the battery chamber 126 may include a cover 132. The cover 132 may be removable or permanent. The cover 132 may be configured to provide access to the batteries 128 and/or hermetically seal the one or more batteries 128 within the battery chamber 126. That is, in a preferred embodiment, the cover 132 and the elongated housing 124 form a hermetic seal when affixed to each other. In one example, the cover 132 may be located about the proximal end 130 of the elongated housing 124.

The interface of the elongated housing 124 with the elongated PCB 116, in a preferred embodiment, forms a hermetic seal to isolate the one or more electronic components 120 within the elongated housing 124. In some instances, the elongated housing 124 may be welded to the elongated PCB 116. In other instances, a biocompatible substance 134, such as a biocompatible epoxy coating (e.g., an epoxy resin) or other biocompatible coating material, may be disposed over at least a portion of the elongated microchip element 112, the elongated PCB 116, and the elongated housing 124. This coating may be multilayered, and it may include a hermetic material so long the material does not interfere with the operation of any of the components, such as the electronic components 120 or the batteries 128.

In certain embodiments, the containment device 110 may include a sleek, tubular profile. For example, some or all of the components associated with the containment device 110 may be elongated. That is, some or all of the components of the containment device 110, such as the elongated microchip element 112, the elongated PCB 116, and the elongated housing 124, may have a greater length than width. Furthermore, the biocompatible coating substance 134, the elongated microchip element 112, and the elongated housing 124 may collectively form a generally circular cross-section and rounded distal end 136 of the containment device 110. The components may collectively fit together to form a sleek, tube-like structure or assembly that may be inserted in a human or animal subject in a minimally invasive manner. The sleek, tube-like structure or assembly preferably has atraumatic surfaces.

The biocompatible coating substance 134 may create an atraumatic surface about the containment device 110. In certain embodiments, the surface of the containment device is formed of or coated with a lubricious substance to facilitate passage of the device to the intended tissue site.

The containment device 110 may be implanted in a human or animal subject, such as a patient in need of treatment, diagnosis, or prophylaxis, by a variety of techniques known in the art. In a preferred embodiment, the device is inserted into the patient at a subcutaneous tissue site. A variety of insertion tools and systems may be used depending on the particular size of the implant and the particular site of implantation desired for a particular medical purpose. The containment device 110 may be inserted, injected, or otherwise placed into the human or animal subject via one or a combination of minimally invasive medical instruments, including a cannula, trocar, subcutaneous insert, or a gun-like injector device or assembly. In one embodiment, a small (e.g., few millimeters) incision is made in the patient's skin, and the containment device 110 is passed through the incision and into the patient just under the skin using a long, narrow inserter tool that can grasp an end of the containment device 110 in a linear low profile arrangement. The containment device 110 would be released from the inserter tool, the end of the inserter tool would be removed from the incision, and then the incision would be closed, for example with one or a few stitches. In some instances, one or more suture loops may be provided with the housing 124 and/or the cap 132. The suture loops may be configured to anchor the containment device 110 in a subcutaneous space.

The electronic components 120 provide any of a number of functions for the containment device 110. Examples include, but are not limited to, a controller (e.g., one or more microprocessors) and power source (e.g., a battery or capacitor) for electrically activating the reservoir 114 to cause it to become opened and/to communicate with a sensor, for example, located within the reservoir 114 or with another device remotely located from the containment device 110. Other electronic components may include, for example, telemetry hardware, capacitors, transistors, and diodes, as well as the control means for actuating the reservoir caps. The control means may include an input source, a microprocessor, a timer, a demultiplexer (or multiplexer). In an embodiment, the electronic components include components for wirelessly receiving energy for charging an on-board storage capacitor, which may further reduce the space requirements for the electronic components on-board the containment device 110. In some instances, the electronic components may include an antenna, such as a transmitter, receiver, or transceiver.

The containment reservoir 114 of the microchip element 112 may be configured to open/activate in a variety of ways, which may be known in the art. In one embodiment, the containment reservoir 114 is structured and configured to be electrically activated to open as described in U.S. Pat. No. 7,510,551 and U.S. Pat. No. 7,604,628, which are incorporated herein by reference.

Figure 4:
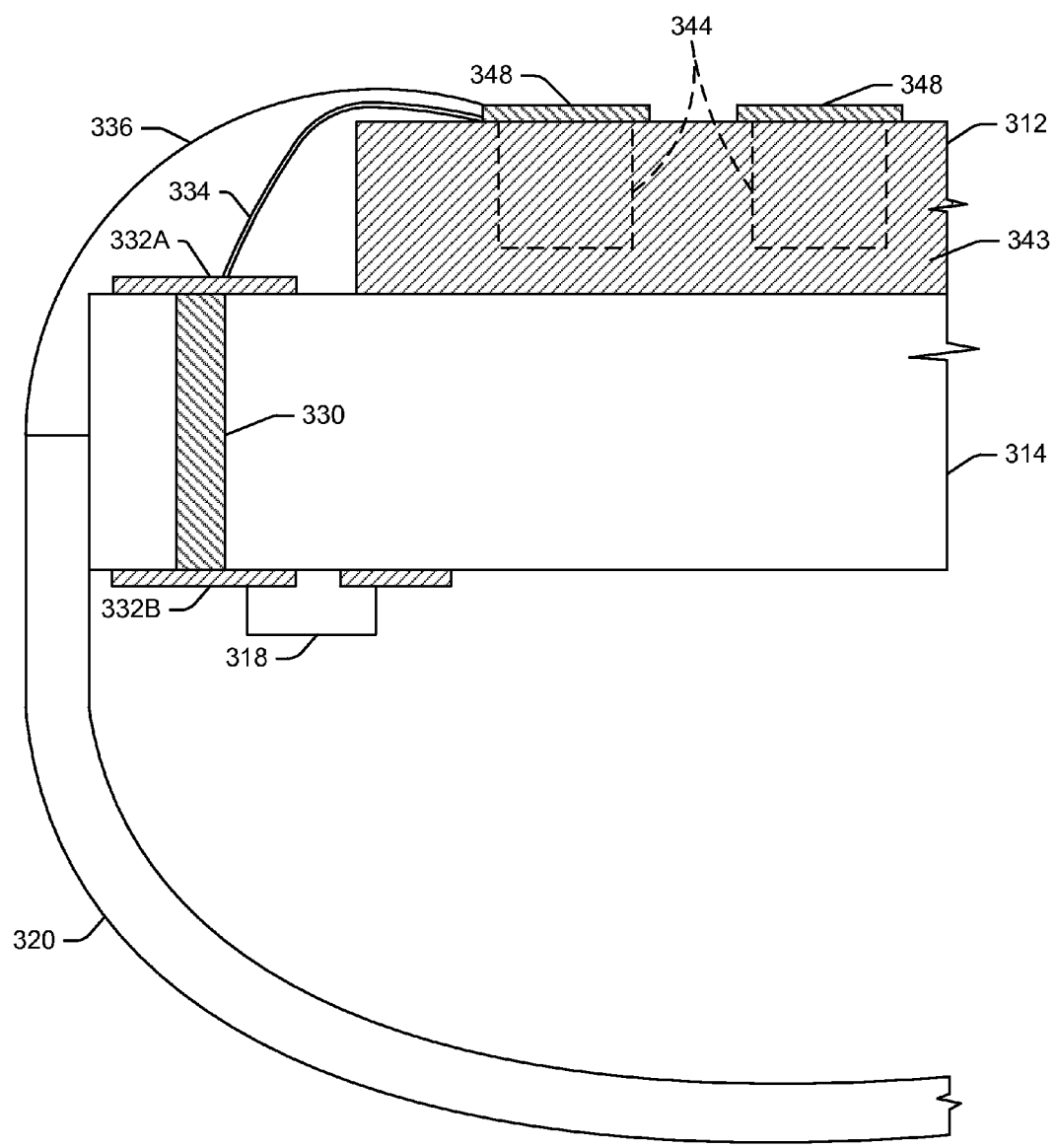
FIG. 4 schematically depicts a close-up, cross-sectional view of a portion of a containment device according to an embodiment.

One embodiment of the electrical connection between a PCB/electronic components and a microchip element is illustrated in FIG. 4. The figure shows part of the microchip element 312 including two containment reservoirs 344. Each containment reservoir 344 has an opening that is (initially) closed off by a reservoir cap 348. The containment reservoir 344, which is formed at least in part in a substrate 343, has a closed end opposed to the opening and a sidewall therebetween. The microchip element 312 is secured to a side of a PCB 314, and electronic component 318 is secured on the opposed side of the PCB 314. The PCB 314 includes a via 330 which electrically connects electronic component 318 to the microchip element 312. Via 330 is mechanically and electrically connected to metallized conductive surfaces 332A, 332B on the PCB 314, and the microchip element 312 is wirebonded 334 to the metallized conductive surface 332A. Any via or wirebond combination may be used. A biocompatible coating substance 336 is applied over the wire bond to secure and protect the connection, and typically will coat part of the surface of the PCB 314, part of the microchip element 312, and part of the housing 320 but not the reservoir caps 348. The coating substance 336 may be a polymer, such as an epoxy or other resin. Any suitable coating may be used.

In one embodiment, the reservoir caps 348 are structured and configured to be electrically activated to open as described in U.S. Pat. No. 7,510,551 and U.S. Pat. No. 7,604,628, which are incorporated herein by reference. That is, in a preferred embodiment, the reservoirs are configured to open by being disintegrated by electrothermal ablation. The reservoir caps 348 may be formed of a metal film, which may comprise a single layer or a laminate structure. For example, the reservoir cap 348 may comprise gold, platinum, titanium, or a combination thereof. In other embodiments, the reservoir cap 348 can be configured to be activated or opened by a mechanical or electrochemical mechanism.

The containment reservoir of the microchip element may be a "microreservoir" which generally refers to a reservoir having a volume equal to or less than 500 µL (e.g., less than 250 µL, less than 100 µL, less than 50 µL, less than 25 µL, less than 10 µL, etc.). In another embodiment, the containment reservoirs may be a "macroreservoir" which generally refers to a reservoir having a volume greater than 500 µL (e.g., greater than 600 µL, greater than 750 µL, greater than 900 µL, greater than 1 mL, etc.) and less than 5 mL (e.g., less than 4 mL, less than 3 mL, less than 2 mL, less than 1 mL, etc.). The terms "reservoir" and "containment reservoir" are intended to encompass both microreservoirs and macroreservoirs unless explicitly indicated to be limited to one or the other.

In another aspect, improved microchip elements and methods for their manufacture are provided. In a preferred embodiment, the microchip device element includes a relatively thin silicon substrate bonded to a relatively thicker primary substrate formed of a polymer or a glass or other ceramic material. Advantageously, by defining the reservoirs in the primary substrate rather than the silicon substrate, the reservoirs may be formed using processes other than dry reactive ion etching (DRIE). This is important, not just because DRIE processes are expensive, but also because under the conventional process, the DRIE processes occurred after deposition of the reservoir cap film, unnecessarily exposing the reservoir cap film to subsequent processing, which can negatively impact the yield of acceptable (e.g., hermetic) reservoir caps.

In addition, by adding the positive sealing features (e.g., gold sealing rings) to the silicon substrate, this keeps all of the high tolerance microfeatures to only the silicon substrate, which in turn advantageously frees up the primary substrate to be made by other, potentially lower tolerance, manufacturing processes. In this way, the reservoir can be made much deeper and thereby increase the unit reservoir payload. In one embodiment, the primary substrate is made by a casting or molding process using ceramic or polymeric materials that allows for formation of reservoirs that are deeper than conventional reservoirs and have smoother side walls than would be readily possible using DRIE. This cast or molded substrate then may be gold plated in and about sealing grooves formed therein for bonding with the positive sealing features on the silicon substrate.

Figure 5A:
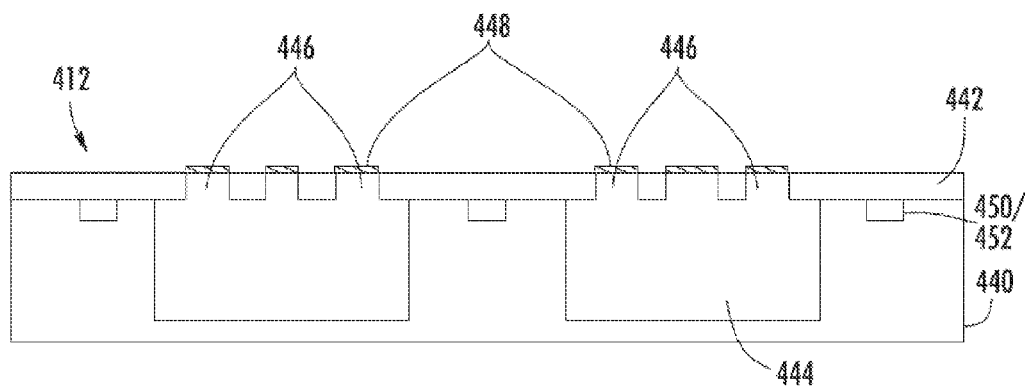
FIG. 5A schematically depicts a cross-sectional view of a microchip element assembly according to an embodiment.
Figure 5B:
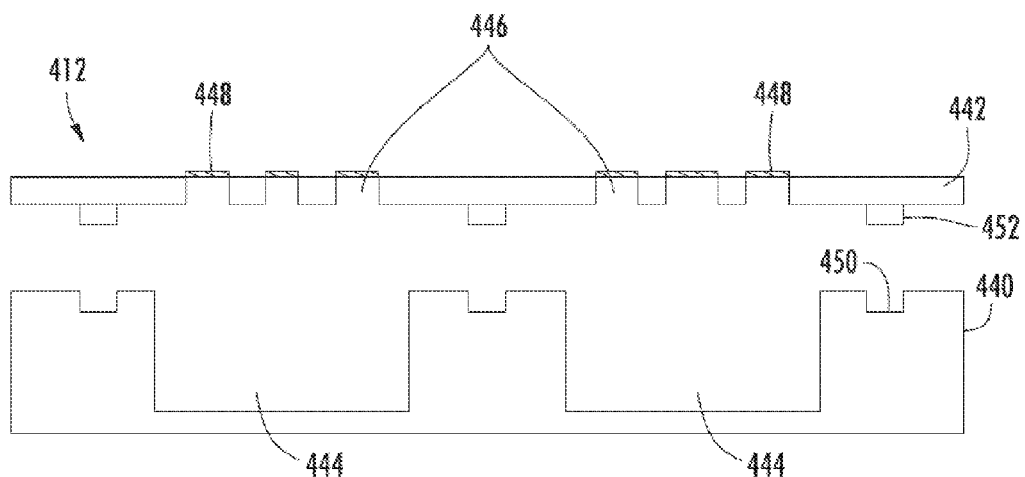
FIG. 5B schematically depicts an exploded cross-sectional view of the microchip element assembly shown in FIG. 5A.

An exemplary embodiment of the elongated microchip element is illustrated in FIG. 5A and FIG. 5B. The elongated microchip element 412 includes a primary substrate 440 and a silicon substrate 442, which are bonded together. The silicon substrate 442 has a first side, an opposed second side, and apertures 446 extending therethrough. Three apertures 446 are shown for each reservoir 444. The first side of the silicon substrate 442 includes reservoir caps 448 which close off the apertures 446 until the reservoir needs to be opened. In a preferred embodiment, the reservoir caps 448 are electrically conductive. For example, the reservoir caps 448 may be in the form of a metal film. The silicon substrate 442, apertures 446, and reservoir caps 448 can be made using microfabrication techniques known in the art. For example, the photolithography, etching, and deposition techniques described in U.S. Pat. No. 7,604,628 may be used to form the apertures 446 in a polysilicon substrate closed off by metal reservoir caps 448.

The primary substrate 440 includes two reservoirs 444 in this illustration, although more or less reservoirs may be included. Each reservoir 444 is defined by a closed end wall, an open end, and at least one sidewall extending between the closed end wall and the open end. As mentioned above, the primary substrate 440 may be formed of silicon. In other embodiments, the substrate may be formed of a metaloid, polymer, glass, or other ceramic material. Any suitable material may be used. The substrate and reservoirs may be made by any suitable process, including but not limited to molding, casting, micromachining, and build-up or lamination techniques known in the art. In one embodiment, the primary substrate 440 is made of/by low temperature co-fired ceramics (LTCC). It may further include a coating layer on all or a portion of the substrate, for example to provide or improve hermeticity, biocompatibility, bonding, and/or reservoir content compatibility, stability, or release. Depending on the purpose of the coating layer, it may be applied inside the reservoirs 444, outside of the reservoirs 444, or both. Examples of possible coating materials include biocompatible metals, such as gold, and polymers, such as parylene.

The primary substrate 440 and the silicon substrate 442 are bonded together using any suitable method, to hermetically seal the reservoirs 444. In this way, the open end of the reservoir 444 is in fluid communication with the apertures 446 for controlled release or exposure of reservoir contents. In a preferred embodiment, the substrates are hermetically sealed together using a compression cold welding process, such as described in U.S. Pat. No. 8,191,756, which is incorporated herein by reference.

As shown in FIGS. 5A and 5B, the second side of the silicon substrate 442 includes ring structures 452 formed thereon, and the first side of the primary substrate 440 includes grooves 450. These bonding features are compressed together to form a cold weld bond hermetic seal surrounding the individual reservoirs 444. The ring structures 452 may be formed by a depositing gold or another metal layer on the silicon substrate 442. The grooves 450 may be etched in the silicon and then coated with a metallized layer of the same material as the metal ring. Variations of this embodiment are envisioned, for example, where other positive and negative bonding features are provided in/on either or both interfacing surfaces of the silicon substrate 442 and the primary substrate 440.

The primary substrate 440 is generally relatively thicker than the silicon substrate 442, and all or at least a majority (greater than 50%) of the reservoir sidewall height (or depth) is defined by the primary substrate 440. In an embodiment, the silicon substrate 442 has thickness that is between 5% and 50% of the thickness of the primary substrate 440 at the bonded interfaces of the substrates.

Although not shown in the FIG. 4 or FIG. 5A, the reservoirs 344 and 444, respectively, include reservoir contents positioned therewithin. The reservoirs can be configured to store essentially any substance or device component in need hermetic containment and subsequent release or exposure at a selected time. The reservoir content may be, for example, a chemical reagent, a drug formulation, or sensor or component thereof, such as an electrode. In an embodiment, a single device includes at least one containment reservoir containing a biosensor and at least one reservoir containing a drug formulation. Examples of various reservoir contents are described for example in U.S. Pat. No. 7,510,551; U.S. Pat. No. 7,497,855; U.S. Pat. No. 7,604,628; U.S. Pat. No. 7,488,316; and PCT WO 2012/027137.

Figure 6:
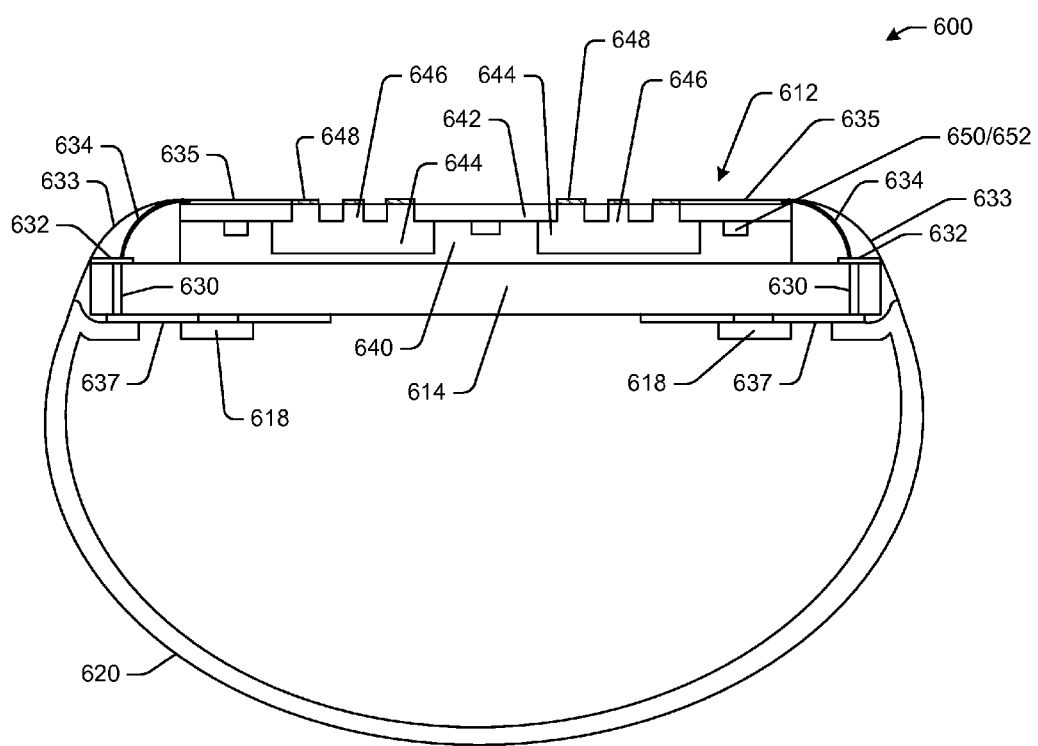
FIG. 6 schematically depicts a cross-sectional close-up view of a portion of an assembled containment device including a microchip assembly according to an embodiment.

An exemplary embodiment of a containment device 600 including a microchip element 612 is illustrated in FIG. 6. The containment device 600 includes a ceramic PCB 614 which has via 630 electrically connecting electronic component 618 to the microchip element 612. The electronic component 618 is secured on a first side of the ceramic PCB 614, and the microchip element 612 is secured on the opposing second side of the PCB 614. The via 630 electrically connects to a metallized conductive surface 632 on the first side of the PCB 614. The electrical circuitry 635 of the microchip element 612 is electrically connected to the metallized surface 632 by a wirebond 634. An epoxy 633 coats the wirebond 634 and at least a portion of the microchip element 612, the ceramic PCB 614, and a housing 620. In this manner, the epoxy 633 ensures that the containment device 600 is void of any atraumatic surfaces. The epoxy 633 also may passivate the wirebond 634. The second side of the ceramic PCB 614 also includes a metallized conductive surface 637, which is electrically connected to the electronic component 618. Although not shown in this illustration, the containment device 600 may include multiple microchip elements, as well as multiple vias, electronic components, and wirebonds. Moreover, the containment device 600 (with the exception of the reservoir caps) may be completely or partially coated by the epoxy 633.

The microchip element 612 includes a primary substrate 640 and a silicon substrate 642. The primary substrate 640 and silicon substrate 642 are bonded together by compression cold welding at/adjacent the interface of a ring structure and groove structure tongue 650/652. Reservoirs 644 are defined in the primary substrate 640 with the open end in fluid communication with apertures 646 defined through the silicon substrate 612. Electrically conductive reservoir caps 648 sealingly cover the apertures 646 and reservoirs 644.

Modifications and variations of the methods and devices described herein will be obvious to those skilled in the art from the foregoing detailed description. Such modifications and variations are intended to come within the scope of the appended claims.

I claim:

1. A containment device, comprising:
   an elongated microchip element comprising one or more containment reservoirs that are configured to be electrically activated to open;
   an elongated electronic printed circuit board (PCB) which comprises a biocompatible and hermetic substrate material, wherein the elongated PCB comprises a first side on which one or more electronic components are fixed and an opposed second side on which the elongated microchip element is fixed in electrical connection to the one or more electronic components without using a feedthrough to operably connect the microchip element to the PCB; and
   an elongated housing fixed to the elongated PCB, wherein the elongated housing and the elongated PCB together form a hermetic enclosure around the one or more electronic components.

2. The containment device of claim 1, wherein at least a portion of the elongated housing comprises a generally cylindrical body.

3. The containment device of claim 1, wherein the elongated housing comprises a battery chamber configured to house one or more batteries therein.

4. The containment device of claim 3, wherein the battery chamber comprises a cover configured to hermetically seal the one or more batteries within the battery chamber.

5. The containment device of claim 1, wherein the elongated housing is formed of a biocompatible metal or alloy.

6. The containment device of claim 1, wherein the biocompatible and hermetic substrate material comprises glass, alumina, or another ceramic.

7. The containment device of claim 1, wherein the elongated PCB comprises at least one via configured to electrically connect at least one of the one or more electronic components to the elongated microchip element.

8. The containment device of claim 7, wherein the at least one via is electrically connected to a metallized conductive surface on the second side of the elongated PCB, and wherein the metallized conductive surface is wirebonded to the elongated microchip element.

9. The containment device of claim 8, wherein a biocompatible coating substance is positioned over the wire bond to secure and protect the connection and create an atraumatic surface about the containment device.

10. The containment device of claim 9, wherein the biocompatible coating substance, the elongated microchip element, and the elongated housing collectively form a generally circular cross-section and rounded distal end of the containment device.

11. The containment device of claim 1, wherein the one or more containment reservoirs comprise microreservoirs containing a drug formulation or a sensor element.

12. The containment device of claim 1, wherein the elongated microchip element comprises:
   a silicon substrate having a first side, an opposed second side, and at least one aperture extending therethrough, wherein the first side of the silicon substrate comprises an electrically conductive reservoir cap which closes off the at least one aperture;
   a primary substrate which is formed of silicon or other metalloid, a polymer, or a glass or other ceramic material, wherein the primary substrate has at least one of the one or more containment reservoirs which is defined by a closed end wall, an open end, and at least one sidewall extending between the closed end wall and the open end; and
   reservoir contents positioned within the at least one of the one or more containment reservoirs,
   wherein the second side of the silicon substrate is hermetically bonded to the primary substrate such that the open end of the reservoir is in fluid communication with the at least one aperture for controlled release or exposure of reservoir contents.

13. The containment device of claim 12, wherein the silicon substrate has a thickness that is between 5% and 50% of the thickness of the primary substrate at the bonded interfaces of the substrates.

14. The containment device of claim 12, wherein the primary substrate comprises a metal coating over at least a part of the polymer, glass or other ceramic material of the primary substrate.

15. The containment device of claim 14, wherein the metal coating coats the at least one sidewall and/or the closed end wall of the at least one of the one or more containment reservoirs.

16. The containment device of claim 12, wherein the second side of the silicon substrate comprises at least one ring structure formed thereon.

17. The containment device of claim 16, wherein the at least one ring structure comprises gold or another metal.

18. The containment device of claim 16, wherein the primary substrate comprises at least one groove structure, wherein the at least one ring structure and the at least one groove structure are configured to form a hermetic bond.

19. The containment device of claim 16, wherein the surface of the primary substrate in and/or adjacent to the at least one groove structure comprises a metal coating.

20. The containment device of claim 19, wherein the metal coating comprises gold.

21. The containment device of claim 1, wherein the elongated housing comprises titanium.

22. A containment device, comprising:
a microchip element comprising one or more containment reservoirs that are configured to be electrically activated to open;
an electronic printed circuit board (PCB) comprising a biocompatible and hermetic substrate, wherein the PCB comprises a first side on which one or more electronic components are fixed and an opposed second side on which the microchip element is directly fixed, without an interposed feedthrough, in electrical connection to the one or more electronic components; and
a housing fixed to the PCB, wherein the housing and the PCB together are configured to hermetically seal the one or more electronic components of the PCB within the housing,
wherein the containment device comprises an elongated tubular structure configured to be injected in a human or animal subject.

23. A method of assembling a containment device, comprising:
providing an elongated microchip element comprising one or more containment reservoirs that are configured to be electrically activated to open;
fixing the elongated microchip element to a first side of an elongated electronic printed circuit board (PCB) which comprises a biocompatible and hermetic substrate without using a feedthrough to connect the elongated microchip element to the PCB;
electrically connecting the elongated microchip element to one or more electronic components which are fixed on a second side of the elongated PCB; and
hermetically sealing the one or more electronic components of the elongated PCB within an elongated housing that is fixed to the elongated PCB.

24. The method of claim 23, wherein providing the elongated microchip element further comprises:
microfabricating a silicon substrate having a first side, an opposed second side, and at least one aperture extending therethrough, wherein the first side comprises an electrically conductive reservoir cap which closes off the at least one aperture;
casting or molding a polymer or a glass or other ceramic material to form a primary substrate having at least one of the one or more reservoirs which is defined by a closed end wall, an open end, and at least one sidewall extending between the closed end wall and the open end;
providing reservoir contents within the at least one of the one or more reservoirs; and
bonding the silicon substrate to the primary substrate such that the open end of the reservoir is in fluid communication with the at least one aperture.

25. The method of claim 24, wherein the silicon substrate has a thickness that is between 5% and 50% of the thickness of the primary substrate at the bonded interfaces of the substrates.

26. The method of claim 24, wherein the microfabricating step further comprises forming at least one ring structure on the second side of the silicon substrate.

27. The method of claim 24, wherein the primary substrate comprises at least one groove structure and the step of bonding comprises compression cold welding the at least one ring structure together with the at least one groove structure.

28. The method of claim 23, wherein the elongated housing comprises a biocompatible metal and the substrate of the PCB comprises glass, alumina, or another ceramic.

* * * * *